(12) United States Patent  (10) Patent No.: US 8,850,662 B2
Gitman et al.  (45) Date of Patent: Oct. 7, 2014

(54) ERGONOMIC HANDLE

(75) Inventors: Eliot Robert Gitman, Jerusalem (IL); David Joseph Hirsch, Jerusalem (IL)

(73) Assignee: Scalpal LLC, Wilmington, DE (US)

( * ) Notice: Subject to any disclaimer, the term of this patent is extended or adjusted under 35 U.S.C. 154(b) by 16 days.

(21) Appl. No.: 12/275,754

(22) Filed: Nov. 21, 2008

(65) Prior Publication Data

US 2010/0005630 A1    Jan. 14, 2010

(30) Foreign Application Priority Data

Jul. 10, 2008  (IL) .......................... 192 739

(51) Int. Cl.
  *B25G 1/10*  (2006.01)
  *A61B 17/3213*  (2006.01)
  *A61B 17/00*  (2006.01)
  *A61C 3/00*  (2006.01)
  *A61B 19/00*  (2006.01)

(52) U.S. Cl.
  CPC ............ *A61B 17/3213* (2013.01); *B25G 1/102* (2013.01); *A61B 2017/00424* (2013.01); *A61C 3/00* (2013.01); *A61B 2019/4868* (2013.01)
  USPC .......................................................... 16/430

(58) Field of Classification Search
  USPC .............. 16/430, DIG. 12, DIG. 19; 606/167; 15/143.1; 30/526, 125; 401/6
  See application file for complete search history.

(56) References Cited

U.S. PATENT DOCUMENTS

| D101,325 S | 3/1870 | Brown |
| 796,980 A * | 8/1905 | Andrews ..................... 15/143.1 |
| 2,173,451 A | 9/1939 | Lorber |
| D134,205 S | 10/1942 | Hasselquist |
| 2,782,764 A | 2/1957 | Lehman, Jr. |
| 3,247,594 A | 4/1966 | Nosonowitz |
| D223,307 S | 4/1972 | Nockolds |
| 4,149,811 A | 4/1979 | Coffman |
| 4,167,347 A | 9/1979 | Hoyle |
| D253,219 S * | 10/1979 | Meyer ........................... D7/693 |

(Continued)

FOREIGN PATENT DOCUMENTS

| EP | 710575 A1 * | 5/1996 | ........... B43K 23/008 |
| WO | 2010/004541 | 1/2010 | |
| WO | 2013/175463 | 11/2013 | |

OTHER PUBLICATIONS

Office Application mailed Feb. 1, 2013 for U.S. Appl. No. 12/620,927, filed Nov. 18, 2009.

(Continued)

*Primary Examiner* — Victor Batson
*Assistant Examiner* — Matthew Sullivan
(74) *Attorney, Agent, or Firm* — Smith, Gambrell & Russell, LLP

(57) ABSTRACT

The invention provides an ergonomic handle for precision, surgical, and dental tools including electro-surgical devices and surgical devices used in microsurgery designed to facilitate the positioning of the user's hand grip comprising a longitudinally extending body substantially oval in cross-section and being provided with four, substantially concave indentations positioned towards the proximal end of the handle, a first concave indentation being provided along a top surface of the handle, second and third indentations being provided along lateral surfaces, and a fourth indentation being provided along the bottom surface of the body respectively and positioned relative to each other to provide a contiguous interface respectively with the user's thumb, index finger and middle finger.

33 Claims, 6 Drawing Sheets

(56) References Cited

U.S. PATENT DOCUMENTS

| | | |
|---|---|---|
| D258,310 S | 2/1981 | LaHaye |
| D269,357 S | 6/1983 | Jagger |
| 4,526,547 A | 7/1985 | Rusk |
| D292,104 S | 9/1987 | Keller, Jr. |
| D298,439 S | 11/1988 | Rusk |
| 4,832,604 A | 5/1989 | Rusk |
| D307,444 S | 4/1990 | Poisson et al. |
| D307,601 S | 5/1990 | Poisson et al. |
| D313,624 S | 1/1991 | Ferjan |
| D318,295 S | 7/1991 | Sze |
| 5,056,945 A | 10/1991 | Klodt |
| 5,143,463 A | 9/1992 | Pozil et al. |
| D330,079 S | 10/1992 | Dalling et al. |
| 5,176,649 A | 1/1993 | Wakabayashi |
| 5,217,001 A | 6/1993 | Nakao et al. |
| 5,228,851 A | 7/1993 | Burton |
| 5,237,984 A | 8/1993 | Williams et al. |
| D359,758 S | 6/1995 | Inami |
| D361,345 S | 8/1995 | Chen |
| 5,440,784 A * | 8/1995 | Hull et al. .................. 16/430 |
| 5,470,162 A | 11/1995 | Rubin |
| D372,047 S | 7/1996 | Adatte et al. |
| 5,531,754 A | 7/1996 | Shackelford, Sr. et al. |
| D373,143 S | 8/1996 | Jagger |
| 5,578,050 A | 11/1996 | Webb |
| 5,626,430 A | 5/1997 | Bistrack |
| 5,785,443 A | 7/1998 | Rubin |
| 5,975,909 A * | 11/1999 | Ritchie .................. 434/127 |
| 5,988,909 A | 11/1999 | Luke, Jr. et al. |
| 6,146,038 A | 11/2000 | Mittersinker et al. |
| D440,605 S | 4/2001 | Izushima |
| 6,296,409 B1 | 10/2001 | Cherry |
| 6,315,476 B2 | 11/2001 | Nakagawa |
| 6,343,885 B1 | 2/2002 | Heyne |
| D457,630 S | 5/2002 | Lehtonen |
| 6,390,818 B2 | 5/2002 | Ferranti |
| 6,408,524 B1 * | 6/2002 | Lai .................. 30/324 |
| 6,502,314 B1 * | 1/2003 | McCatty .................. 30/340 |
| 6,554,515 B2 | 4/2003 | Debbas |
| D480,423 S | 10/2003 | Kung |
| 6,752,555 B2 | 6/2004 | Geddes et al. |
| D499,141 S | 11/2004 | Chevalier |
| D504,700 S | 5/2005 | Chuang |
| D512,458 S | 12/2005 | Shiina |
| D515,389 S * | 2/2006 | Hsu .................. D8/83 |
| 7,101,382 B2 | 9/2006 | George et al. |
| D533,944 S | 12/2006 | Sullivan et al. |
| 7,150,754 B2 | 12/2006 | Ziemer |
| 7,153,317 B2 | 12/2006 | Kanodia et al. |
| D535,749 S | 1/2007 | Yaniv et al. |
| 7,240,390 B2 * | 7/2007 | Pfenniger et al. .................. 15/22.1 |
| D560,803 S | 1/2008 | Tasse et al. |
| D561,828 S | 2/2008 | Wesselmann |
| D565,106 S | 3/2008 | Silverstein |
| 7,357,773 B2 * | 4/2008 | Watschke .................. 600/29 |
| D568,475 S | 5/2008 | Sandel et al. |
| D589,619 S * | 3/2009 | Wu .................. D24/147 |
| D590,062 S | 4/2009 | Wu |
| 7,647,704 B2 | 1/2010 | Peterson |
| D620,107 S | 7/2010 | Bartlett et al. |
| D632,391 S | 2/2011 | Gitman |
| D633,142 S | 2/2011 | Chaffee et al. |
| D635,260 S | 3/2011 | Gitman |
| D642,214 S | 7/2011 | Gitman |
| D651,648 S | 1/2012 | Luettgens |
| D660,421 S | 5/2012 | Miller et al. |
| 8,434,954 B2 | 5/2013 | Gitman et al. |
| D687,950 S | 8/2013 | Gitman |
| 2002/0124353 A1 * | 9/2002 | Holland-Letz .................. 16/430 |
| 2002/0170145 A1 * | 11/2002 | Stvartak et al. .................. 16/430 |
| 2004/0133217 A1 * | 7/2004 | Watschke .................. 606/148 |
| 2004/0204629 A1 | 10/2004 | Knapp |
| 2005/0150083 A1 * | 7/2005 | Roberts .................. 16/430 |
| 2005/0155185 A1 * | 7/2005 | Shmueli et al. .................. 16/430 |
| 2006/0026800 A1 * | 2/2006 | Lawless .................. 16/430 |
| 2006/0041266 A1 * | 2/2006 | Sullivan et al. .................. 606/167 |
| 2006/0075606 A1 * | 4/2006 | Lawless .................. 16/430 |
| 2006/0252989 A1 | 11/2006 | Bar-Or et al. |
| 2006/0263142 A1 | 11/2006 | Goldberg |
| 2007/0156160 A1 * | 7/2007 | Petersen .................. 606/167 |
| 2008/0051813 A1 * | 2/2008 | Dunn .................. 606/167 |
| 2008/0163463 A1 * | 7/2008 | Hulden .................. 16/430 |
| 2009/0187069 A1 | 7/2009 | Terliuc et al. |
| 2010/0095487 A1 | 4/2010 | Gitman |
| 2011/0087070 A1 | 4/2011 | Tilson et al. |
| 2012/0010468 A1 | 1/2012 | Afridi |

OTHER PUBLICATIONS

Office Action issued by the USPTO on Sep. 13, 2013 in continuation U.S. Appl. No. 12/620,927.

Office Action dated Apr. 25, 2012 in continuation-in-part application of U.S. Appl. No. 12/620,927.

Office Action dated Mar. 26, 2012 in continuation-in-part application of U.S. Appl. No. 12/605,729.

* cited by examiner

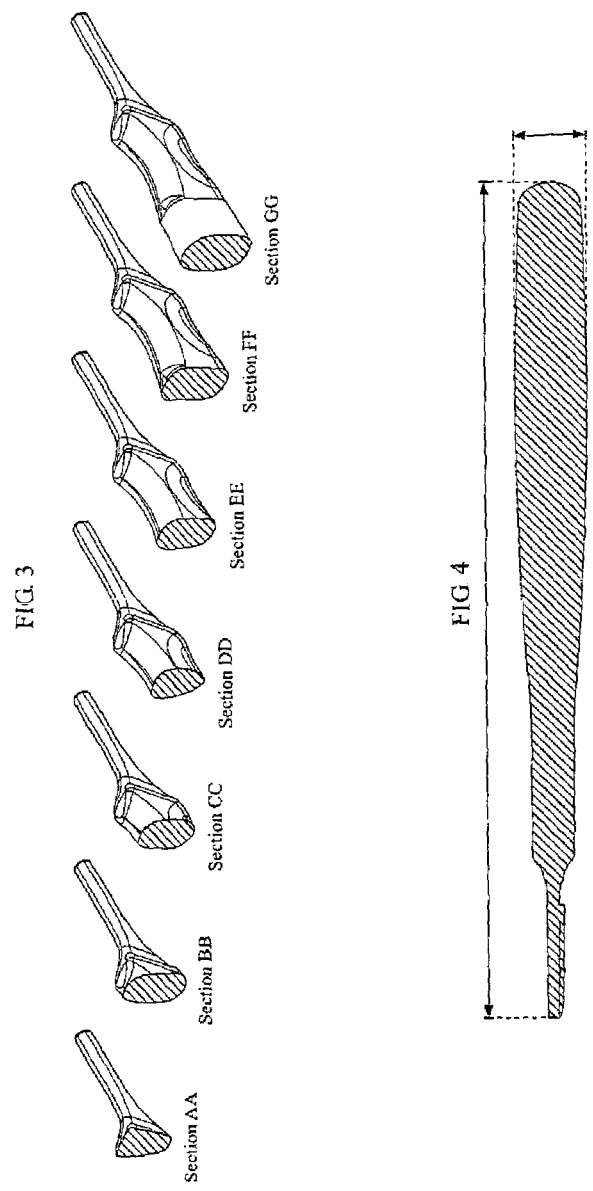

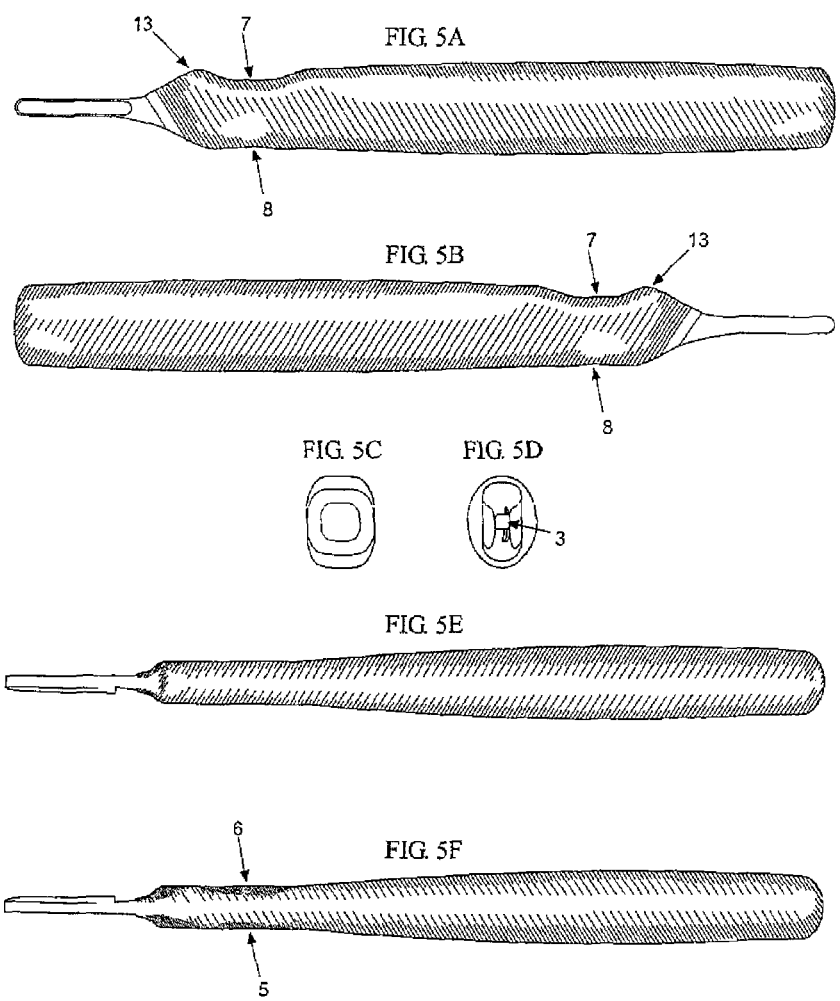

ERGONOMIC HANDLE

TECHNICAL FIELD

The present invention relates to handles. More particularly, the invention relates to handles for precision, surgical, and dental tools including electro-surgical devices and surgical devices used in microsurgery.

BACKGROUND OF THE INVENTION

Standard scalpel handles with flat gripping arrangements do not provide contoured gripping surfaces to keep the index finger, thumb and middle finger in place. Moreover, standard scalpel handles with flat body handle gripping arrangements can lead to slippage of the fingers onto the blade or an uncontrolled rolling between the fingers.

Many innovative scalpel handle designs have been implemented in order to address issues related to ergonomic requirements of a scalpel grip. Thus, there have been several scalpel designs to address the protection of the scalpel user from the danger of the sharp blade.

U.S. Pat. No. 5,531,754 to Shackelford, Sr. et al describes a retractable blade mounted on a blade holder mechanism housed within a cover housing. The blade holder mechanism includes a resilient spring clip that is biased against the sheath.

U.S. Pat. No. 7,101,382 to George et al comprises a retractable scalpel device with two releasable latching elements. When the scalpel blade is in an extended position, each releasable latching element is accessible for depression by finger pressure to cause retraction of the extended blade. The releasable latching elements are located on opposite edges (top and bottom) of a cover housing and about halfway along its length. The releasable latching elements must be depressed at the same time for the extended scalpel blade to be retracted into the housing.

U.S. Pat. No. 7,153,317 B2 to Kanodia et al comprises a disposable guarded surgical scalpel, which includes a handle with a blade fixed to it and a sliding mounted guard. When the scalpel is in use, the guard is moved to a retracted position where the blade is exposed: the guard locks in this position. When not in use the guard is moved to an extended position where the blade is covered. The guard has grooves on the outer surface to provide a better grip for the surgeon.

U.S. Design Pat. No. D101,325 to Brown is directed to a new, original and ornamental design for a scalpel. The design is characterized by the configuration of the handle wherein the walls and upper edge are transversely grooved or serrated in conjunction with the tapering beveled upper and lower edges.

U.S. D535,749 attributable to Yaniv et al depicts an ornamental design for a scalpel.

U.S. Pat. No. 5,578,050 to Webb is directed to a rubber sleeve for use over a scalpel handle.

U.S. Design Pat. No. D457,630 S to Lehtonen is directed to a scalpel handle which makes no provision for indentations for the positioning of the fingers.

U.S. Pat. No. 7,150,754 to Ziemer is directed to the alignment of a scalpel blade without the necessity for eye contact. To achieve this object the invention proposes a handle region comprising three lateral faces, which are disposed such that a cross section with a triangular envelope results for the handle region, and at least one of the lateral faces is provided with tactile identifying features. The triangular envelope of the cross section of the handle region facilitates a proper holding of the scalpel blade holder between middle finger, thumb and index finger, the scalpel blade holder and thus the scalpel fixed thereto being able to assume only three different rotational states about the center axis of the handle region of the scalpel blade holder, with respect to the fingers. The limitation in movement to only three rotational states allows the user to determine the alignment of the scalpel blade holder and of the scalpel affixed thereto via his fingers by means of his sense of touch. The handle has an arc-triangular shape. The rounded corners contribute to a better grip, and in addition prevent the user from hurting himself on the corners or damaging protective gloves, and do not need to be dimensioned as big as tactile identifying features designed as recesses.

US Patent Application 2006/0041266 to Sullivan et al comprises a distal section of a surgical scalpel handle which has an enlarged finger pressure section. This section is about one third of the length of the entire handle and has small protrusions at its right and left sidewalls. The finger pressure section has a slight bottom curvature and an indentation at its top face. The indentation is as wide and long as a pad of an adult index finger i.e. the pad from the tip of the index finger to the first knuckle. The top face of the finger pressure section is wider than the top face of the body section. The body section of the handle is triangular. The right side face and the left side face form a "V," or an acute angle of 20-60 degrees having a tip line.

Flat or triangular shaped devices are not comfortable for the user, as these handles do not sufficiently cater to the ergonomic requirements of a grip. Flat body handles provide textured gripping surfaces for the fingers, but are too small or too narrow to grip comfortably for extended periods of time, or once gripped restrict the free movement of the hand. Furthermore, flat body handle gripping arrangements can only be used basically in one position without the danger of slippage or rolling between the fingers accompanied by the risk of consequent injury to the user or the patient. Grips having triangular cross-sections may present an ease of orientation positioning, however, they fall short of providing ergonomically comfortable working solutions. One edge of the triangular shaped device can dig into a user's finger.

While alleviating many of the problems related to efficiently using a scalpel, such as positioning and maintaining a desired grip, the grips disclosed in the prior art do not address the need to minimize the fatigue due to the need to adjust relative position of fingers and maintain an assured operational control and alignment of the scalpel blade during surgery, and, furthermore, these grips do nothing to eliminate the need for additional personnel to maintain whatever mechanical, or sanitary features of the prior art.

SUMMARY OF THE INVENTION

Therefore the objectives of the present invention are to obviate the disadvantages of prior art scalpel handles and to provide a scalpel handle which has uniquely spaced indentations that accommodate finger form rather than finger pressure allowing the scalpel handle to be gripped comfortably for long periods of time, allowing the handle to be gripped in alternative positions, unhindered by either dry or wet gloves, providing simplicity of manufacture, and requiring minimal or no maintenance.

It is a further object of the present invention to provide scalpel handle which has four molded concave indentations proximal to the operational end of the instrument, further having an oval shape with an additional user index finger support, significantly facilitating precise surgical operations.

The present invention achieves the above objectives by providing an ergonomic handle for precision, surgical, and dental tools designed to facilitate the positioning of the user's finger grip comprising a longitudinally extending body substantially oval in cross-section and being provided with four, substantially concave indentations positioned towards the proximal end of the handle, a first concave indentation being provided along a top surface of the handle, second and third indentations being provided along lateral surfaces, and a fourth indentation being provided along a bottom surface of the body, said indentations being positioned relative to each other to provide a contiguous interface respectively with the user's thumb, index finger and middle finger.

In a preferred embodiment of the present invention there is provided an ergonomic handle wherein the surface area of the top of the handle is contoured such that extending from its distal end toward its proximal end and approaching the proximal end there is provided a concave indentation which extends and merges into an elevated ridge-like surface support which tapers angularly towards the proximal end of the handle.

In another preferred embodiment of the present invention there is provided an ergonomic handle wherein the four indentations are spaced about 90° apart from each other.

In a further preferred embodiment of the present invention there is provided an ergonomic handle wherein the longitudinally extending body has an axis and the first concave indentation is cut deeper into the body towards the axis than at least one of the other indentations.

In a further preferred embodiment of the present invention there is provided an ergonomic handle wherein the handle is provided with the means at its proximal end for attachment thereto of interchangeable surgical blades and instruments along the longitudinal axis.

In yet a further preferred embodiment of the present invention there is provided an ergonomic handle wherein the ridge-like surface support is both elevated and has a projecting convex curve so as to allow for positioning of the user's index finger sufficiently close to the proximal end of the handle body while preventing the index finger from slipping toward the proximal end.

In a most preferred embodiment of the present invention there is provided an ergonomic handle wherein the surgical tool is a scalpel.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

BRIEF DESCRIPTION OF THE DRAWINGS

In the drawings:

FIG. 3 is an exploded multi-sectional perspective view of the sections in FIG. 2;

FIG. 4 is a top, cross-section view of the handle according to the invention;

FIG. 5A is a left side view of the handle according to the invention, showing the dorsal indentation and bottom indentation;

FIG. 5B is a right side view of the handle according to the invention, showing the dorsal indentation and bottom indentation;

FIG. 5C is the distal end view of the handle according to the invention;

FIG. 5D is the proximal end view of the handle according to the invention, showing the shank thereof;

FIG. 5E is the top view of the handle according to the invention;

FIG. 5F is the bottom view of the handle according to the invention, showing the lateral indentations;

DETAILED DESCRIPTION OF CERTAIN EMBODIMENTS OF THE INVENTION

Figure 1:
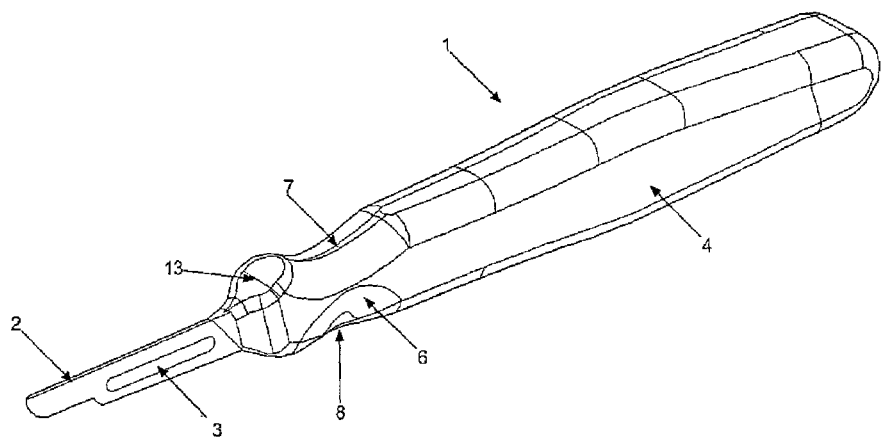
FIG. 1 is a perspective view of a preferred embodiment of the handle according to the invention.

There is seen in FIG. 1 a surgical scalpel handle 1 for use in conjunction with a disposable surgical blade 2 attachable to a shank 3 extending longitudinally from the proximal end of the handle 1. The handle 1 comprises a longitudinally extending body 4 which is substantially oval in cross-section and is formed of sequential ovals of varying width and shape. The handle has four concave indentations 5 (not visible), 6, 7, and 8 moldably formed thereinto, and adjoining the proximal end of the handle 1.

According to one embodiment of the present invention, the indentations 5 and 6 are designed to accommodate the middle finger and the thumb, respectively, and the indentations 7 and 8 are designed to generally accommodate the index finger and the middle finger respectively, thereby facilitating gripping by a user. Thus, the user fingers are free from being confined to the grip positions of the handle when in use. The general configuration of the indentation according to the embodiment of the invention allows for the user to comfortably grip the handle 1 in various gripping positions.

Figure 6A:
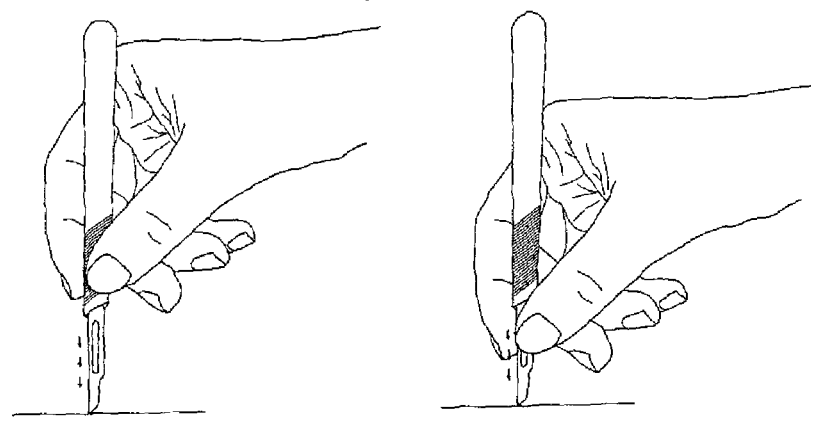
FIG. 6A illustrates the danger of a finger slipping and sustaining an injury when using a standard scalpel handle.
Figure 6B:
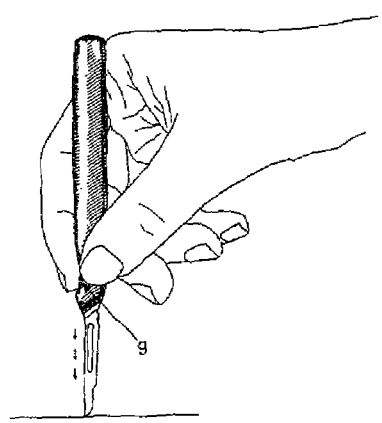
FIG. 6B illustrates the use of the handle according to the invention, thereby preventing the slipping of the finger.

According to one embodiment of the invention, the top indentation 7 as illustrated in FIGS. 1, 5A, and 5B is designed to accommodate the index finger 9 of a right handed user, as seen in FIG. 6B, engaging most of the ball and tip thereof. The lateral indentation 6 as illustrated in FIG. 1 and FIG. 5F is designed to accommodate the thumb 10 of the user, as seen in FIG. 7B, engaging most of the ball thereof. The bottom indentation 8 as illustrated in FIGS. 1, 5A, and 5B, is designed to accommodate a portion of the middle finger 11 of the user, as seen in FIG. 7B, at the first joint on a side adjoining the positioning of the index finger. The lateral indentation 5 as illustrated in FIG. 5F, is designed to accommodate a portion of the middle finger 12 of the user, as seen in FIG. 7B. The positioning of the lateral indentations is reversed in the case of a left-handed user. Thus, the accommodation of the lateral indentations for the middle finger and the thumb, involve the engagement of the same parts of the said middle finger and thumb as detailed above in respect to the right handed user.

The top concave indentation 7 shown in FIGS. 1, 5A, and 5B has a preferred maximum depth of about 2.0 mm below the surface of the handle, which is preferably slightly deeper than the lateral indentations 5 and 6 as shown in FIG. 5F which have a preferred maximum depth of about 1.0 mm and the bottom indentation 8 as shown in FIGS. 1 and 5A which has a preferred maximum depth of about 0.3 mm at its lowest point.

In FIGS. 1, 5A, and 5B there is also seen an additional ridge-like surface support 13 which acts as an abutment for index finger of the user, thereby providing an assured grip into the soft pad of the finger and to prevent slippage when cutting and performing close up work. The ridge-like surface support 13 is disposed at the front face of the proximal end of the handle and forms a curve to the highest and proximal point of the top indentation. The midpoint of the ridge-like surface support 13 is seen in section AA in FIG. 2 having a preferred horizontal length of about 6.1 mm and a preferred vertical height of about 9.2 mm.

Figure 2:
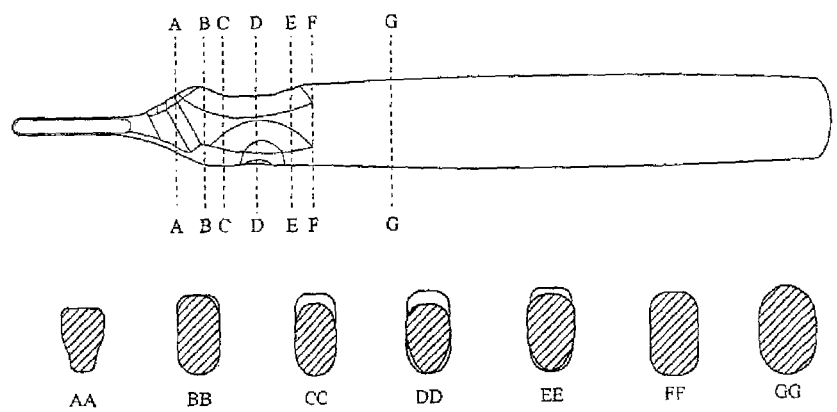
FIG. 2 is a side view of the handle and sectional views thereof.

There is seen in FIG. 2 a cross section A-A disposed at the foremost point of the ridge-like surface support 13 and most proximally to the proximal end of the handle 1, and the characteristic pear shape thereof is also shown in FIG. 3. The section A-A has a preferred vertical height of about 9.2 mm and a preferred horizontal width of about 6.1 mm. The section B-B is disposed at the second end point of the top concave indentation 7 closest to the front of the handle as depicted in FIG. 2 and its characteristic shape is illustrated in FIG. 3. The section B-B has a preferred vertical height of about 11.5 mm and a preferred horizontal width of about 6.2 mm. Although the sections A-A and B-B are disposed transversely and generally on the same longitudinal axis of the handle 1, there are nevertheless significant differences in both the height and width of the two sections; the height differential thereof being preferably about 2.3 mm and the width differential being preferably about 0.1 mm. This difference allows for the comfort and accuracy required for the index finger when disposed upon the top indentation 7.

Section C-C is disposed along the downslope curve and inward to the top concave indentation as illustrated in FIG. 2 and the characteristic shape thereof is also shown in FIG. 3. The section CC has a preferred vertical height of about 10.6 mm and a preferred horizontal width of about 6.3. The section D-D is disposed at a middle point along the top concave indentation 7 as illustrated in FIG. 2 and the characteristic shape thereof is also shown in FIG. 3. The section D-D has a preferred vertical height of about 9.7 mm and a preferred horizontal width of about 6.5. The section E-E is disposed along the upslope curve towards the top of the concave indentation 7 as illustrated in FIG. 2 and the characteristic shape thereof is also shown in FIG. 3. The section E-E has a preferred vertical height of about 11 mm and a preferred horizontal width of about 6.7. The section F-F is disposed at the highest point on the top of the concave indentation 7 as illustrated in FIG. 2 and the characteristic shape thereof is shown in FIG. 3. The section F-F has a preferred vertical height of about 12 mm and a preferred horizontal width of about 7 mm. The section G-G is substantially along the middle of the shank 3 of the handle 1 as illustrated in FIG. 2 and the characteristic shape thereof is shown in FIG. 3. The section G-G has a preferred vertical height of about 12.7 mm and a preferred horizontal width of about 8.4 mm.

The two lateral concave indentations 5 and 6 accommodating the user thumb and middle finger, respectively, are depicted in FIGS. 1 and 5F, and constitute mirror images of each other, in respect of measurement, shape and size. Notwithstanding the fact that the engagement of the thumb has a wider and broader surface area as compared to the middle finger, according to one embodiment of the invention the identical dimensions of the lateral indentations assure equal facility for both. The bottom indentation 8, as seen in FIGS. 1, 5A, and 5B allows for the follow-through, or comfortable interchangeability of the middle finger of the user from the lateral indentation to the bottom indentation. In other words, the four indentations are substantially axially aligned.

FIG. 6A illustrates the danger of finger slippage and accompanying consequent injury to the user or the patient when using standard scalpel handles as compared to the safety of the unique design of the present invention which prevents finger slippage as depicted in FIG. 6B.

Figure 7A:
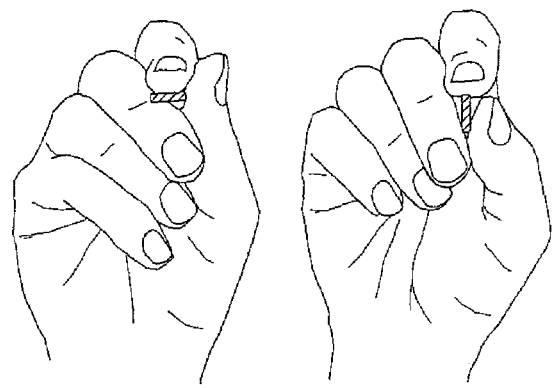
FIG. 7A illustrates a cross-section of a hand-held prior art handle and the lack of control when a standard scalpel handle is rotated between the fingers.
Figure 7B:
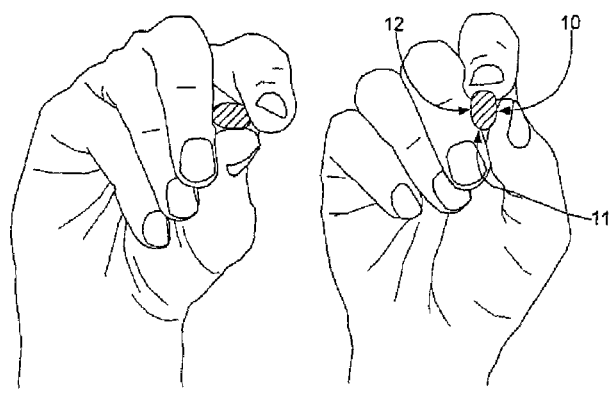
FIG. 7B illustrates a cross-section of a hand-held handle and the use of the handle according to the invention when it is rotated between the fingers.

FIG. 7B illustrates the advantageous maneuverability of the handle in the present invention when compared to the standard scalpel shape as depicted in FIG. 7A. The handle design, form and characteristic ergonomic grip featured in the present invention, and discussed hereabove facilitate more contact with the handle, providing gradual adjustment from vertical and horizontal surfaces of the handle, allow for safe close up work, and reduces the possibility of sudden finger slippage or uncontrollable rolling between the user fingers. Moreover, the configuration of the handle of the present invention allows the user to rotate the handle without the handle rolling over uncontrollably, and further allows the user to effortlessly control the handle while the handle remains stable.

The present invention allows for a closer anchoring of the user's pinky finger as a support for greater precision work. The closer the user's grip is to the front of the handle for close up work, the easier are his opportunities to effectively use the instrument.

Figure 8A:
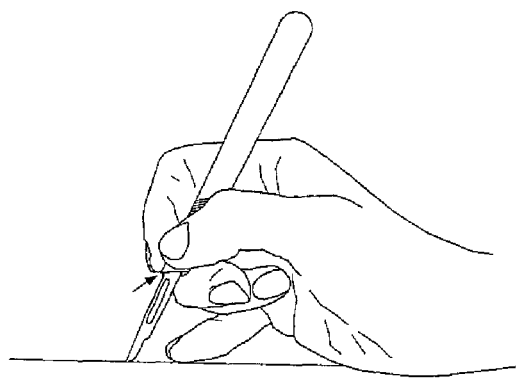
FIG. 8A illustrates the higher hand grip position on the standard scalpel handle of the prior art.
Figure 8B:
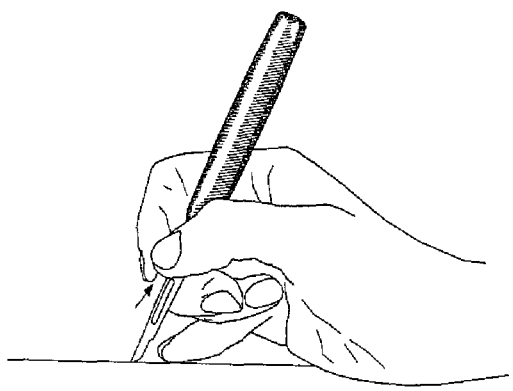
FIG. 8B illustrates the lower hand grip position on the handle according to the invention.

Thus, FIG. 8A illustrates the necessity for a higher, or undesired finger grip position, in relation to the cutting area, to be maintained when using a scalpel of standard design of the prior art. The lower finger grip position on the handle of the present invention allows for a comfortable finger grip extension beyond the limits of the indentations in the handle as depicted in FIG. 8B.

Moreover, rather than employing a textured grip known for the softness or porosity thereof making sterilization difficult, the handle of the present invention is manufactured of non-textured materials, according to one embodiment of the invention, thereby creating a form grip which is easy to sterilize.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An ergonomic handle comprising a longitudinally extended body provided on its outer surface with four, substantially concave indentations that include a first concave indentation provided along a top surface of said body, which first concave indentation extends and merges into an elevated ridge surface support that is proximally positioned relative to the first concave indentation, second and third indentations being provided along lateral surfaces of the body, and a fourth indentation being provided along the bottom surface of said body, and wherein the body comprises, along a longitudinal length of said body, a plurality of sequential oval cross-sections of varying width and shape and each with an oval major diameter axis extending in a top to bottom direction, and wherein said indentations are positioned relative to each other to provide a contiguous interface relative to the user's thumb, index finger and middle finger to facilitate controlled rolling between the user's fingers, and wherein said second and third indentations are more predominantly located on lower portions of the lateral surfaces.

2. The handle according to claim 1 wherein the four indentations are spaced about 90° apart from each other, with the second and third indentations each having an upper portion aligned with a minor axis of the cross-section and a maximum depth positioned in the lower portion of the lateral sides.

3. The handle according to claim 1 wherein said body has a central axis and said first concave indentation is cut deeper into said body towards said axis than at least one of said other indentations.

4. The handle according to claim 1 wherein said handle is a precision instrument handle configured for use with a precision instrument selected from the group consisting of ball point pen, a felt-tipped pen, a fountain pen, a pencil, a mechanical pencil, a rapidiograph, a computer stylus; a scoring instrument, an engraving tool, and a soldering device.

5. The handle according to claim 1 wherein said handle is a precision instrument handle configured for use with a precision instrument selected from the group consisting of a surgical tool, a dental tool, an electro-surgical tool and a microsurgery tool.

6. The handle according to claim 1 wherein said handle is a precision instrument handle configured for use with a precision instrument that is a scalpel.

7. The handle according to claim 1, wherein said first, top indentation is formed on a top portion of said body so as to define a top curved end portion in a vertical cross-sectional plane extending perpendicular to a central axis of said body, and said fourth, bottom indentation is formed on a bottom portion of said body so as to also define a curved end portion in the vertical cross-sectional plane.

8. The handle according to claim 1, wherein at least one of the second and third lateral indentations extends into the bottom indentation such that said at least one of said second and third lateral indentations and said bottom indentation define together a continuous middle finger reception cavity comprised of a portion of that one of the lateral indentations and a portion of the bottom indentation, and said top indentation is configured for accommodating an index finger of said user, and the other of said lateral indentations is configured for accommodating a thumb of said user.

9. The handle according to claim 1, wherein one of the lateral indentations is configured for accommodating both a portion of a middle finger and a thumb of a user, said top indentation being configured for accommodating a further portion of said middle finger of said user, the other of said lateral indentations being configured for accommodating an index finger of said user and said bottom indentation being configured for accommodating said thumb of said user.

10. The handle according to claim 1, wherein one of the second and third lateral indentations is configured for accommodating a portion of a thumb of a user, said top indentation being configured for accommodating a portion of a middle finger and a further portion of said thumb of said user, the other of said lateral indentations being configured for accommodating a further portion of said middle finger of said user and said bottom indentation being configured for accommodating an index finger of said user.

11. The handle according to claim 1, wherein one of the second and third lateral indentations is configured for accommodating an index finger of a user, said top indentation being configured for accommodating a portion of a thumb of said user, the other of said lateral indentations being configured for accommodating a portion of a middle finger and a portion of said thumb of said user, and said bottom indentation being configured for accommodating a further portion of said middle finger of said user.

12. The handle according to claim 1, wherein said top indentation has a maximum depth of 2.0 mm below a surface of the body, said lateral indentations have a maximum depth of 1.0 mm below a surface of the body, and said bottom indentation has a maximum depth of about 0.3 mm below a surface of the body.

13. The handle according to claim 1, wherein said top indentation is concave and extends from a distal end of said body toward a proximal end of said body, and wherein said elevated ridge surface support has a proximal side tapering angularly down towards said proximal end of said handle.

14. The handle according to claim 1, wherein the interface between an upper end of one of the second and third indentations and the top indentation is contiguous across a lateral side, longitudinally extending ridge region representing a maximum outer surface of the lateral side.

15. The handle according to claim 1, wherein a distance between opposing, interior-most surfaces of said first and fourth concave indentations is greater than a lateral spacing distance of said second and third lateral surfaces at a common axial location on said body.

16. The handle according to claim 1, wherein, on opposing sides of a horizontal cross-section plane extending through the lateral second and third sides and along a longitudinal central axis of extension of said body, there is defined a non-symmetrical relationship in the oval cross-section positioned at the maximum depth of the first concave indentation.

17. An ergonomic handle comprising a longitudinally extended body provided on its outer surface with four, substantially concave indentations that include a first concave indentation being provided along a top surface of said body, which first concave indentation extends and merges into an elevated ridge surface support, second and third indentations being provided along lateral surfaces, and a fourth indentation being provided along the bottom surface of said body, and wherein a distance between opposing, interior-most surfaces of said first and fourth concave indentations is greater than a lateral spacing distance of said second and third lateral surfaces at a common axial location on said body, and wherein said body comprises a plurality of sequential oval cross-section of varying width and shape, and wherein said indentations are positioned relative to each other to provide a contiguous interface relative to the user's thumb, index finger and middle finger to facilitate controlled rolling between the user's fingers, and wherein said second and third indentations each have a maximum depth positioned in a respective lower half of the lateral sides.

18. The handle according to claim 17, wherein, on opposing sides of a horizontal cross-section plane extending through the lateral second and third sides and along a longitudinal central axis of extension of said body, there is defined a non-symmetrical relationship in the oval cross-section positioned at the maximum depth of the first concave indentation.

19. A handle comprising a longitudinally extended body provided on its outer surface with four, substantially concave indentations that include a first concave indentation being provided along a top surface of said body, which first concave indentation extends and merges into an elevated ridge surface support, second and third indentations being provided along lateral surfaces, and a fourth indentation being provided along the bottom surface of said body, and wherein, on opposing sides of a horizontal cross-section plane extending through the lateral second and third surfaces and along a longitudinal central axis of extension of said body, there is defined a non-symmetrical relationship in the oval cross-section positioned at the maximum depth of the first concave indentation; and wherein said body comprises in sequence along the longitudinal axis of extension, a plurality of oval cross-sections of varying width and shape, and wherein said indentations are positioned relative to each other to provide a contiguous interface relative to the user's thumb, index finger and middle finger to facilitate controlled rolling between the user's fingers, and wherein, relative to the oval cross-section positioned at the maximum depth of the first concave indentation, the bottom side of the oval cross-section converges inward more than the top side.

20. The handle according to claim 19, wherein the second and third indentations are positioned predominately in the bottom side of the oval cross section positioned at the maximum depth of the first concave indentation and converge with the bottom indentation such that there is provided a common, extended middle finger reception region comprising a portion of one of said second and third indentations and a portion of the fourth indentation and a thumb reception region comprising the other of said second and third indentations and another portion of the fourth indentation.

21. The handle according to claim 19, wherein lateral side portions defining the second and third indentations, in the oval cross-section positioned at the maximum depth of the first concave indentation, converge downwardly toward one another to merge with the bottom indentation and to also, together, define a continuous bottom curve within the oval cross-section at the maximum depth of the first concave indentation.

22. The handle according to claim 21, wherein the interface between an upper end of one of the second and third indentations and the top indentation is contiguous across a lateral side, longitudinally extending ridge region representing a maximum outer surface of the lateral side.

23. The handle according to claim 17, wherein lateral side portions defining the second and third indentations, in the oval cross-section positioned at the maximum depth of the first concave indentation, converge downwardly toward one another to merge with the bottom indentation and to also, together, define a continuous bottom curve within the oval cross-section at the maximum depth of the first concave indentation.

24. The handle according to claim 23, wherein the interface between an upper end of one of the second and third indentations and the top indentation is contiguous across a lateral side, longitudinally extending ridge region representing a maximum outer surface of the lateral side.

25. An instrument comprising the handle of claim 19 and a tool device extending out away from a proximal end of said handle.

26. The instrument of claim 25, wherein the tool device includes a detachable tool member supported by said handle.

27. The instrument of claim 26, wherein said detachable tool member is a blade.

28. The instrument of claim 27, wherein the blade is a scalpel blade.

29. An instrument comprising the handle of claim 1, wherein said tool device includes a shank, and a tool member supported by said shank.

30. The instrument of claim 25, wherein the instrument is a precision instrument selected from the group consisting of a ball point pen, a felt-tipped pen, a fountain pen, a pencil, a mechanical pencil, a rapidiograph, a computer stylus; a scoring instrument, an engraving tool, and a soldering device.

31. The instrument of claim 25, wherein the instrument is a precision instrument selected from the group consisting of a surgical tool, a dental tool, an electro-surgical tool and a microsurgery tool.

32. The instrument of claim 25, wherein only the proximal end of the handle has a tool device extending from the handle.

33. The handle according to claim 19, wherein the oval cross-section, positioned at the maximum depth of the first concave indentation, is positioned closer to a proximal end to the body than a distal end of the body.

* * * * *